US00PP11279P

United States Patent [19]

Gilford et al.

[11] Patent Number: Plant 11,279

[45] Date of Patent: Mar. 7, 2000

[54] STRAWBERRY PLANT NAMED 'MIRADOR'

[75] Inventors: Kristie L. Gilford, Dover, Fla.; Amado Q. Amorao, Camarillo, Calif.; Bruce D. Mowrey, La Selva Beach, Calif.; Thomas M. Sjulin, Aromas, Calif.

[73] Assignee: Driscoll Strawberry Associates, Inc., Watsonville, Calif.

[21] Appl. No.: 08/862,821

[22] Filed: May 23, 1997

[51] Int. Cl.[7] ..... A01H 5/00

[52] U.S. Cl. ..... Plt./209

[58] Field of Search ..... Plt./49, 48, 208, Plt./209

[56] References Cited

U.S. PATENT DOCUMENTS

P.P. 1,745 8/1958 Lang ..... Plt./49
P.P. 7,024 9/1989 Johnson, Jr. et al. ..... Plt./49
P.P. 8,649 3/1994 Sjulin ..... Plt./48
P.P. 9,909 6/1997 Ackerman et al. ..... Plt./49

*Primary Examiner*—Howard J. Locker
*Assistant Examiner*—Kent L. Bell
*Attorney, Agent, or Firm*—Pennie & Edmonds LLP

[57] ABSTRACT

This invention relates to a new and distinct variety of strawberry plant named 'Mirador', botanically identified as *Fragaria×ananassa* Duch. The closest known variety is 'Commander'. The new variety is a day-neutral fruit bearing variety. The new variety is characterized from 'Commander' by its globose plant habit, strong interveinal leaf-blistering, sparse to medium petiole pubescence, moderate to marked difference in fruit shape between primary and secondary fruit, absent or very narrow fruit band without achenes, dark red fruit skin color, medium fruit glossiness, smaller to same size of calyx in relation to the fruit, medium to late time of flowering, mid-season to late time of fruiting, and day-neutral type of fruit bearing.

3 Drawing Sheets

BACKGROUND OF THE INVENTION

The new variety of strawberry plant was selected as a seedling in a controlled breeding plot at a ranch in Ventura County, Calif., U.S.A., on or about October 1994. The new variety originated as a result of a controlled cross between the strawberry plants named 'Irvine', U.S. Plant Pat. No. 7,172, and 'Key Largo', U.S. Pat. No. 8,649, in an on-going breeding program. The seedling of the new variety was grown and asexually propagated by stolons at the nursery of Driscoll Strawberry Associates, Inc., in McArthur, Shasta County, Calif. The new variety was further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Mirador' (formerly known as 'DX-5'). The variety is botanically identified at *Fragaria×ananassa* Duch. Among the characteristics which distinguish the new variety from other varieties of which we are a combination of traits which include plant habit, interveinal leaf blistering, petiole pubescence, the difference in fruit shape between primary and secondary fruit, band on fruit without achenes, fruit skin color, fruit glossiness, size of calyx in relation to the fruit, time of flowering, time of fruiting, and type of bearing.

COMPARISON TO CLOSEST VARIETIES

The variety which we believe to be closest to 'Mirador' from those known to us is 'Commander' (U.S. Plant Pat. No. 7,024). There are several characteristics of the new variety that are different from, or not possessed by 'Commander'. For example, the plant habit of 'Mirador' is globose, while that of 'Commander' is flat globose. The interveinal blistering of the leaves of 'Mirador' is strong, while that of 'Commander' is weak. The petiole pubescence of 'Mirador' is sparse to medium in density, while that of 'Commander' is dense. The difference in fruit shape between primary and secondary fruit for 'Mirador' is moderate to marked, while that of 'Commander' is none or very slight. The band on the Fruit without achenes of 'Mirador' is absent or very narrow, while that of 'Commander' is narrow. The fruit skin color of 'Mirador' is dark red, while that of 'Commander' is orange red. The fruit glossiness of 'Mirador' is medium, while that of 'Commander' is strong. The size of the calyx in relation to the fruit of 'Mirador' is smaller to the same size, while that of 'Commander' is the same size to larger. The time of flowering of 'Mirador' is medium to late, while that of 'Commander' is early to medium. The time of fruiting of 'Mirador' is mid-season to late, while that of 'Commander' is early to medium. Lastly, 'Mirador' is a day-neutral fruit bearing variety, while 'Commander' is partially everbearing.

Regarding isozyme analysis, the phosphoglucoisomerase (PGI) isozyme banding pattern for 'Mirador' is A3 while that for 'Commander' is A4 . The leucine aminopeptidase (LAP) isozyme banding pattern for 'Mirador' is B3, with the slower migrating band staining more weakly than typical in others possessing the B3 pattern, while that for 'Commander' is B3. The phosphoglucomutase (PGM) isozyme banding pattern for 'Mirador' and 'Commander' is C4. All isozyme analyses were conducted using leaf tissue. See *J. Amer. Soc. Hort. Sci.* 106:684 (1981).

TABLE 1

Isozyme Analysis for 'Mirador' and Commander'

| Locus | Cultivar 'Mirador' | Cultivar 'Commander' |
|---|---|---|
| PGI | A3 | A4 |
| LAP | B3* | B3 |
| PGM | C4 | C4 |

The 'Commander' isozyme data is from U.S. Plant Pat. No. 7,024.
*B3 with the slower migrating band staining more weakly than typical in others possesssing the B3 pattern.

BRIEF DESCRIPTION OF THE ILLUSTRATIONS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
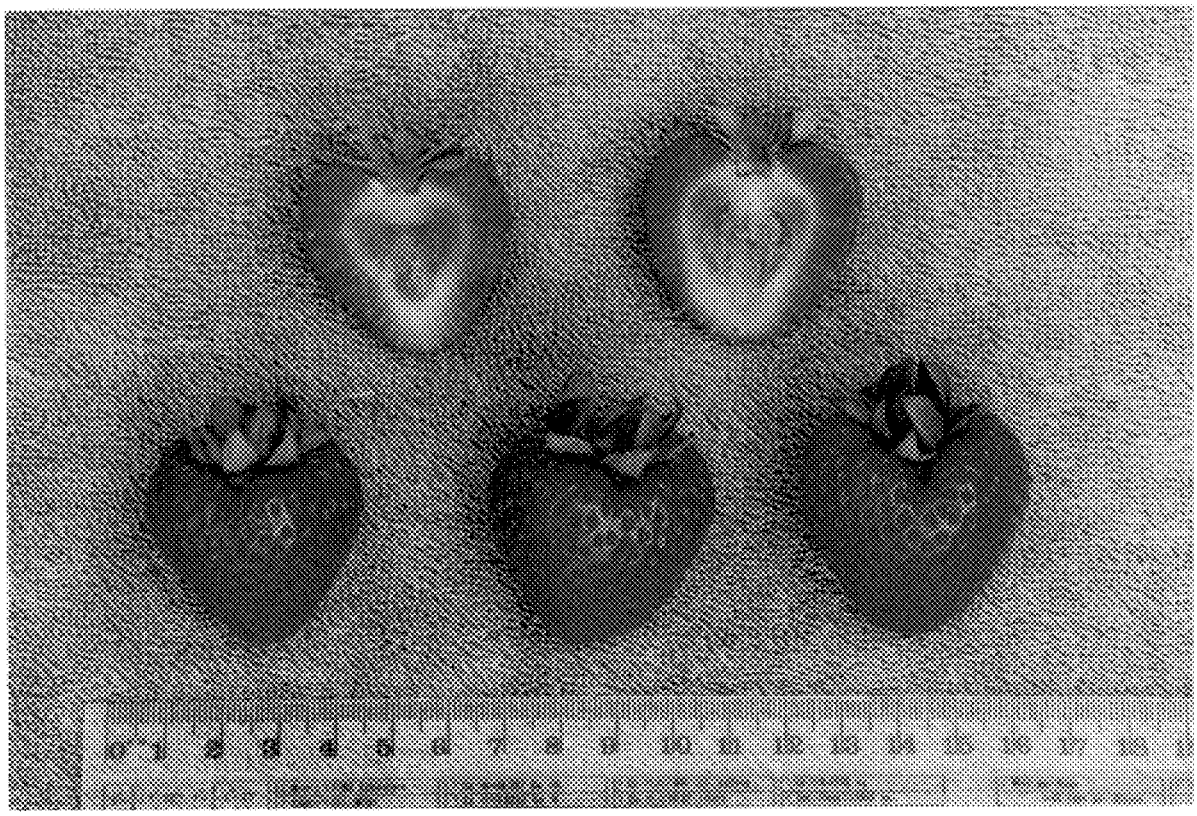
FIG. 1 shows typical whole fruit and the fruit in longitudinal section, illustrating the typical flesh and flesh coloration, core and shape of the new variety.
Figure 2:
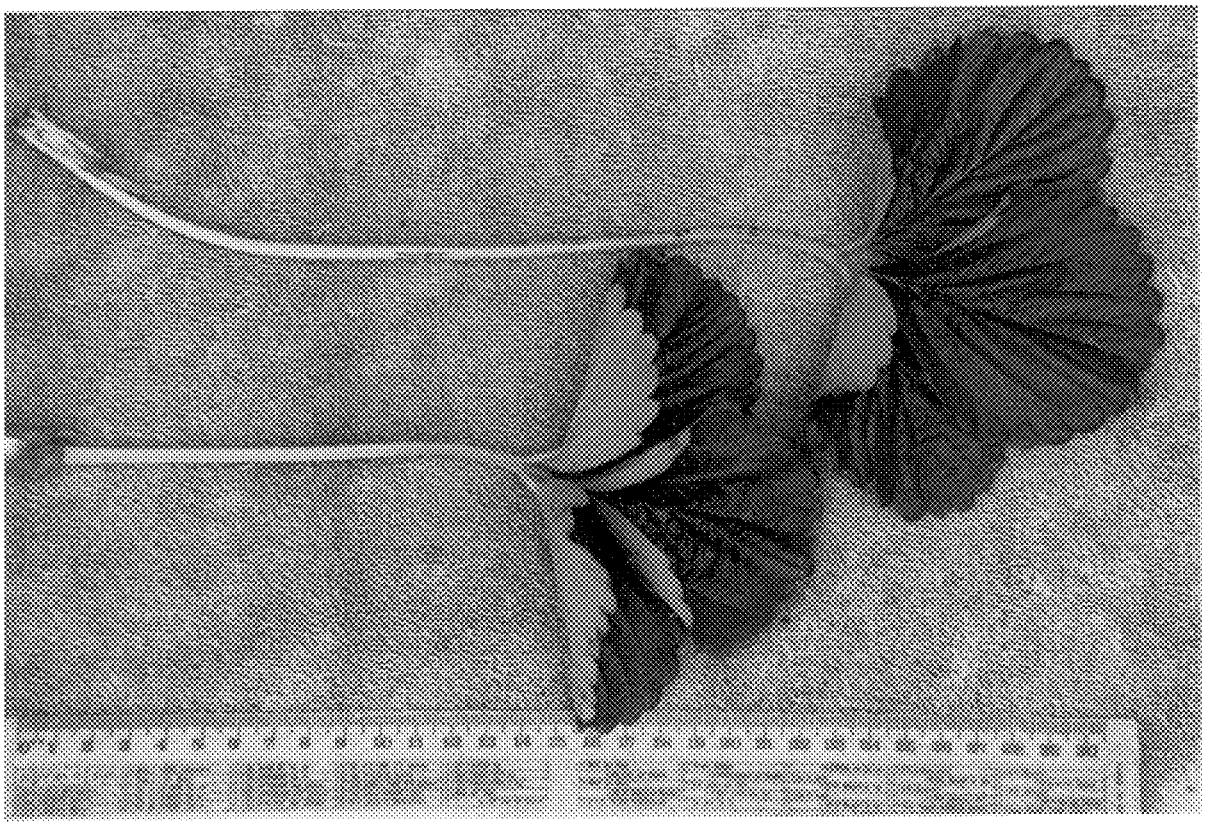
FIG. 2 shows the upper surface of two typical folioles of the new variety.
Figure 3:
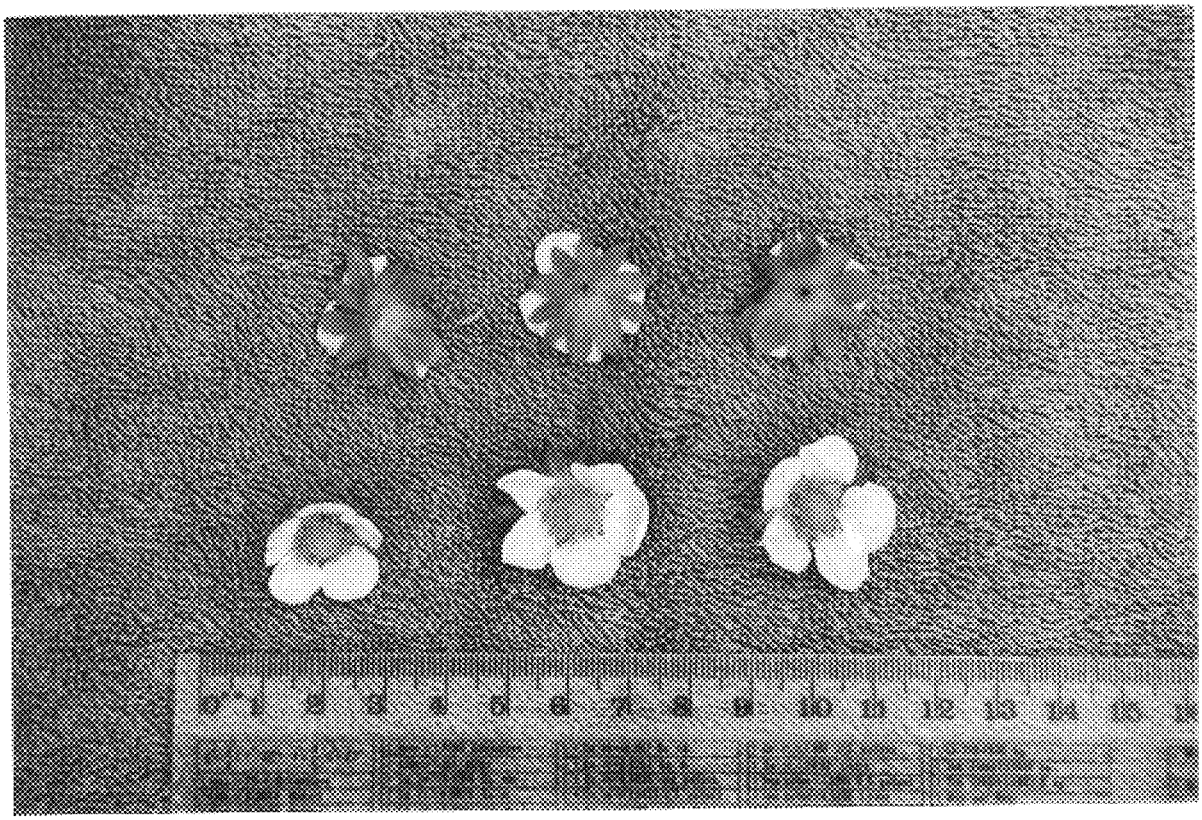
FIG. 3 shows the flowers and reproductive organs of the new variety, as well as the size and position petals and sepals.

The following detailed description of the new variety is based upon observations taken of plants and fruit grown in experimental test plots in 1997 at the J&D ranch in Santa Cruz County, Calif., U.S.A. The plant material was planted in the fall of 1996 and grown in a forcing system. Observations of 'Mirador' and 'Commander' were taken in a side-by-side comparison in May 1997. Additional measurements were taken in Florida during the 1997–98 and 1998–99 growing seasons. This description is in accordance with UPOV terminology. Color designations, color descriptions, and other phenotypical descriptions may deviate from the stated values and descriptions depending upon variation in environmental, seasonal, climatic and cultural conditions. Colors are described using standard Munsell Notation.

Propagation

The new variety is principally propagated by way of stolons. Although propagation by stolons is presently preferred, other known methods of propagating strawberry plants may be employed.

Characteristics of the New Variety

The following information is provided to describe the new variety.

Plant: The plants are of open to medium density with globose habit and strong vigor. Specifically, at fruiting the average height and average width of 'Mirador' are 13.5 cm and 28.1 cm, respectively.

Leaves: The upperside of the leaves are medium to dark green with a Munsell color rating of 2.9GY 2.3/3.6. The underside of the leaves are gray-green which is not included on the Munsell color cascade.

The leaf profile is concave to slightly concave and there is strong interveinal leaf-blistering. Plants have three leaflets only. The leaflet shape is oval to slightly spatulate. The terminal leaflet margin profile is flat and the length-to-width ratio of the terminal leaflet is as long as broad. The leaves have medium glossiness. The shape of the base of the terminal leaflet is rounded and the teeth of the terminal leaflet are rounded. The shape of the terminal leaf apex is rounded. The average terminal leaflet width of 'Mirador' is 7.6 cm. The average terminal leaflet length of 'Mirador' is 7.7 cm. The venation of the leaflets is pinnate.

The petiole has sparse to medium pubescence and the pose of the petiole hairs is outwards to slightly upwards. The average petiole length of 'Mirador' is 9.2 cm. The average petiole diameter of 'Mirador' 0.5 cm. The Munsell color rating for petiole color of 'Mirador' is 3.7GY 6.0/10.7.

Stolons: 'Mirador' has a medium number of stolons that are of medium thickness to thick with weak to medium anthocyanin coloration and medium pubescence.

Inflorescence: The position of the inflorescence is from level with to above the foliage. The flowers are medium in size. The average flower diameter is 3.6 cm. The aspect or appearance of the flower of 'Mirador' has the typical look and shape of the species. The petal color is white which is not included on the Munsell color cascade. The anther color has a Munsell color rating of 1.6Y 7.7 /15.4. The average petal length of 'Mirador' is 1.4 cm. The average petal width is 1.6 cm. The texture of the petals is smooth.

The diameter of the calyx is about the same size as the corolla. The average calyx diameter is 3.9 cm. On secondary flowers, the diameter of the inner calyx is the same size as the outer calyx. On secondary flowers with 5 to 6 petals, the petals are touching to overlapping. The petal length-to-width ratio on secondary flowers is broader than they are long.

The fruiting trusses are medium to long in length and the attitude at first picking is semi-erect. The average number of flowers per fruiting truss of 'Mirador' is 2.92. The average yield for 'Mirador' in the 1997–1998 fruiting season was 314g of fruit/plant. The yield of 'Mirador' is above average compared to other varieties. The fruiting truss of 'Mirador' is moderate to highly branched.

Fruit: Observations of the fruit were taken of secondary fruit on one year old plants. Strawberry plants possess a branching inflorescence, or peduncle, having a primary (first) flower which is the largest and secondary flowers which are on the lateral branches. "Secondary fruit" are those that develop from secondary flowers which develop from lateral buds on the peduncle. One year old plants are those which are in their first year in the fruiting field. The fruit are predominantly conical in shape. The fruit ratio of length to maximum width is as long as broad. The fruit are medium to large in size. The average length and diameter of the fruit is 3.4 cm and 2.4 cm, respectively. The average weight of the fruit is 17.7g/ berry as measured in the 1997–1998 fruiting season. There is a moderate to marked difference in fruit shape between the primary and secondary fruits. The average length and width of the primary fruit are 4.0 cm, respectively. The average length/width ratio of the primary fruit is 1.18. The band without achenes is absent or very narrow. The fruit surface has a weak unevenness.

Fruit Color: The fruit skin color is slightly uneven to even dark red with a Munsell color rating of 7.5R 2.1/6.1 and medium glossiness. The insertion of the achenes is from level with the surface to above the surface of the fruit. The achenes are yellow (Munsel color rating 9.1YR 7.3/15.7) but darken to a red color when exposed to sunlight (Munsell color rating 6.7R 3. /13.1) The calyx is inserted from in a basin to level with the fruit and the pose of the calyx segments is reflexed. The calyx diameter is from smaller to the same size as the fruit diameter. The adherence of the calyx to the fruit is strong.

The fruit flesh is firm when fully ripe. The color of the fruit flesh is orange red with a Munsell color rating of 7.0R 4.3/16.4. The fruit flesh color is slightly uneven, and the fruit flesh color distribution is marginal and central. The fruit has a medium sized hollow center.

The fruit has a medium to strong sweetness, with weak to medium acidity and medium texture.

The time of flowering when 50% of the plants are at first flower is medium to late.

The harvest maturity when 50% of the plants possess ripe fruit is mid-season to late.

'Mirador' is a day-neutral bearing variety. Day-neutral bearing strawberry varieties are characterized as plants for which flowering is unaffected by photoperiod. See *J. Amer. Soc. Hort. Sci.* 109(3):396-400 (1984).

Chilling Requirements: 'Mirador' has only been tested extensively in Florida in a green plant system. In this system, plants are transplanted from the nursery to the fruiting field with the leaves intact. Chilling is not a requirement is this system.

Resistance to Stress

The new variety 'Mirador' is moderately resistant to high pH and high soil salt levels.

Disease Resistance and Susceptibility

The 'Mirador' fruit is moderately susceptible to decay by Botrytis fruit rot. 'Mirador' is moderately susceptible to leaf spots (*Xanthomonus fragariae*).

The 'Mirador' variety is moderately susceptible to injury by *Tetranychus urticae*. The 'Mirador' variety is susceptable to injury by *Tarsonemus pallidus, Aphis spp.,* and *Lygus hesperus*.

What is claimed is:

1. A new and distinct variety of strawberry plant, substantially as shown and described.

* * * * *